US011939570B2

(12) United States Patent
Rausch et al.

(10) Patent No.: US 11,939,570 B2
(45) Date of Patent: *Mar. 26, 2024

(54) MICROFLUIDIC LAB-ON-A-CHIP FOR GENE SYNTHESIS

(71) Applicant: Seagate Technology LLC, Fremont, CA (US)

(72) Inventors: Tim Rausch, Farmington, MN (US); Walter R Eppler, Cranberry Township, PA (US); Gemma Mendonsa, Minneapolis, MN (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 495 days.

This patent is subject to a terminal disclaimer.

(21) Appl. No.: 16/857,006

(22) Filed: Apr. 23, 2020

(65) Prior Publication Data

US 2021/0054364 A1 Feb. 25, 2021

Related U.S. Application Data

(60) Provisional application No. 62/889,400, filed on Aug. 20, 2019.

(51) Int. Cl.
| | | |
|---|---|---|
| *C12N 15/10* | (2006.01) | |
| *B01L 3/00* | (2006.01) | |
| *C40B 60/14* | (2006.01) | |
| *G06F 12/02* | (2006.01) | |
| *G11C 13/02* | (2006.01) | |
| *G16B 50/30* | (2019.01) | |

(52) U.S. Cl.
CPC ........ *C12N 15/1031* (2013.01); *B01L 3/5027* (2013.01); *C12N 15/1065* (2013.01); *C12N 15/1093* (2013.01); *C40B 60/14* (2013.01); *G06F 12/02* (2013.01); *G11C 13/02* (2013.01); *G16B 50/30* (2019.02)

(58) Field of Classification Search
CPC ............ C12N 15/1031; C12N 15/1065; B01L 3/5027
See application file for complete search history.

(56) References Cited

U.S. PATENT DOCUMENTS

| | | | |
|---|---|---|---|
| 6,287,825 | B1 | 9/2001 | Weissman et al. |
| 10,260,087 | B2 | 4/2019 | Coll Mulet et al. |
| 2006/0141626 | A1 | 6/2006 | Hauge et al. |
| 2007/0196834 | A1 | 8/2007 | Cerrina et al. |
| 2008/0044893 | A1* | 2/2008 | Pollack ................... C30B 29/58 422/63 |
| 2011/0124049 | A1* | 5/2011 | Li ....................... C12N 15/1031 435/91.2 |
| 2011/0166044 | A1* | 7/2011 | Jones ................ B01L 3/502738 506/37 |

FOREIGN PATENT DOCUMENTS

| | | |
|---|---|---|
| WO | 2009/020435 A1 | 2/2009 |
| WO | 2016/065300 A1 | 4/2016 |
| WO | WO-2018236889 A2 * 12/2018 | .......... B01J 19/0046 |

OTHER PUBLICATIONS

Kong, David S., et al., "Parallel gene synthesis in a microfluidic device," Nucleic Acids Research, 2007, vol. 35, No. 8.

* cited by examiner

*Primary Examiner* — Sahana S Kaup
(74) *Attorney, Agent, or Firm* — HOLZER PATEL DRENNAN

(57) ABSTRACT

A microfluidic lab-on-a-chip system for DNA gene assembly that utilizes a DNA symbol library and a DNA linker library. The lab-on-a-chip has a fluidic platform with a plurality of arrays operably connected to a voltage source and a controller for the voltage source, a set of first inlets operably connected to the fluidic platform, each first inlet for one DNA symbol from a DNA symbol library, a set of second inlets operably connected to the fluidic platform, each second inlet for one DNA linker from a DNA linker library, and a mixing area operably connected to the fluidic platform and to the plurality of first inlets and the plurality of second inlets.

10 Claims, 13 Drawing Sheets

Specification includes a Sequence Listing.

```
        ┌─ 10a                          ┌─ 10b
        ↙                                ↙
TCGATTCCGATCGATTCCGT            CGTATTCCGATCGATTCAAA
AGCTAAGGCTAGCTAAGGCA            GCATAAGGCTAGCTAAGTTT
```

FIG. 1A

```
                ┌─ 100a                          ┌─ 100b
                ↙         ┌─ 104a                ↙
102a ┐                                    
      ATTCCGATCGATTCCGT             ATTCCGATCGATTCAAA
      AGCTAAGGCTAGCTAAG           ┌GCATAAGGCTAGCTAAG
                            102b ┘                    ┐
                                                       └ 104b
```

FIG. 1B

```
                        ┌─ 1000
                        ↙
100a ┐                                  ┌─ 100b
      ↘                                  ↙
      ATTCCGATCGATTCCGT│ATTCCGATCGATTCAAA
      AGCTAAGGCTAGCTAAG│GCATAAGGCTAGCTAAG
```

TCGATTCCGG
TTAGCTAAGG

500b

CGTATTCCGG
TTGCATAAGG

500c

CGAAATCCGG
TTGCTTTAGG

FIG. 5A 502a   504a   500a                         506a

CCAT + TAAA + TCGATTCCGG  =  TAAATCGATTCCGGCCAT
CCGG     AT    TTAGCTAAGG     ATTTAGCTAAGGCCGG 502b   504b   500b                         506b

CCGT + TAAA + CGTATTCCGG  =  TAAACGTATTCCGGCCGT
CCGG    TAAT   TTGCATAAGG     TAATTTGCATAAGGCCGG 502c   504c   500c                         506c

CC  + TAAA + CGAAATCCGG  =  TAAACGAAATCCGGCC
CCGG   CAAT   TTGCTTTAGG     CAATTTGCTTTAGGCCGG

TAAATCGATTCCGGCATTAAACGTATTCCGGCCGTTAAACGAAATCCGGCC
ATTTAGCTAAGGCCGGTAATTTGCATAAGGCCGGCAATTTGCTTTAGGCCGG

FIG. 5C

╭─ 708a
TAAATCGATTCCGGCCATTAAACGTATTCCGGCCGTTAAACGAAATCCGGCCTC
ATTTAGCTAAGGCCGGTAATTTGCATAAGGCCGGCAATTTGCTTTAGGCCGG

TAAATCGATTCCGGCCATTAAACGTATTCCGGCCGTTAAACGAAATCCGGCC
AGATTTAGCTAAGGCCGGTAATTTGCATAAGGCCGGCAATTTGCTTTAGGCCGG
                                                                    ╰─ 708b

FIG. 7C

708a ⟶  TAAATCGATTCCGGCC...TAAACGAAATCCGGCCTC
        ATTTAGCTAAGGCCGG...ATTTGCTTTAGGCCGG

+

708b ⟶  TAAATCGATTCCGGCC...TAAACGAAATCCGGCC
        AGATTTAGCTAAGGCCGG...ATTTGCTTTAGGCCGG

=

TAAATCGATTCCGGCC...TAAACGAAATCCGGCCTCTAAATCGATTCCGGCC...TAAACGAAATCCGGCC
ATTTAGCTAAGGCCGG...ATTTGCTTTAGGCCGGAGATTTAGCTAAGGCCGG...ATTTGCTTTAGGCCGG

SEQUENCE LISTING

```
<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Example nucleotide sequence as illustrated in
      FIG. 1A

<400> SEQUENCE: 1
```

```
tcgattccga tcgattccgt                                          20

<210> SEQ ID NO 2
<211> LENGTH: 20
<212> TYPE: DNA
<213> ORGANISM: Artificial Sequence
<220> FEATURE:
<223> OTHER INFORMATION: Example nucleotide sequence as illustrated in
      FIG. 1A

<400> SEQUENCE: 2
cgtattccga tcgattcaaa                                          20

<210> SEQ ID NO 3
<211> LENGTH: 17
<212> TYPE: DNA
<213> ORGANISM: Artificial Sequence
<220> FEATURE:
<223> OTHER INFORMATION: Example nucleotide sequence as illustrated in
      FIG. 1B.

<400> SEQUENCE: 3
agctaaggct agctaag                                             17

<210> SEQ ID NO 4
<211> LENGTH: 17
<212> TYPE: DNA
<213> ORGANISM: Artificial Sequence
<220> FEATURE:
<223> OTHER INFORMATION: Example nucleotide sequence as illustrated in
      FIG. 1B.

<400> SEQUENCE: 4
attccgatcg attccgt                                             17

<210> SEQ ID NO 5
<211> LENGTH: 17
<212> TYPE: DNA
<213> ORGANISM: Artificial Sequence
<220> FEATURE:
<223> OTHER INFORMATION: Example nucleotide sequence as illustrated in
      FIG. 1B.

<400> SEQUENCE: 5
gcataaggct agctaag                                             17

<210> SEQ ID NO 6
<211> LENGTH: 17
<212> TYPE: DNA
<213> ORGANISM: Artificial Sequence
<220> FEATURE:
<223> OTHER INFORMATION: Example nucleotide sequence as illustrated in
      FIG. 1B.

<400> SEQUENCE: 6
attccgatcg attcaaa                                             17

<210> SEQ ID NO 7
<211> LENGTH: 20
<212> TYPE: DNA
<213> ORGANISM: Artificial Sequence
<220> FEATURE:
<223> OTHER INFORMATION: Example nucleotide sequence as illustrated in
      FIG. 2.

<400> SEQUENCE: 7
```

-continued tcgattccgg ttagctaagg                                              20

<210> SEQ ID NO 8
<211> LENGTH: 19
<212> TYPE: DNA
<213> ORGANISM: Artificial Sequence
<220> FEATURE:
<223> OTHER INFORMATION: Example nucleotide sequence as illustrated in
      FIG. 2.

<400> SEQUENCE: 8
cgtattccgg ttgctaagg                                               19

<210> SEQ ID NO 9
<211> LENGTH: 52
<212> TYPE: DNA
<213> ORGANISM: Artificial Sequence
<220> FEATURE:
<223> OTHER INFORMATION: Example nucleotide sequence as illustrated in
      FIG. 5c.

<400> SEQUENCE: 9
taaatcgatt ccggccatta aacgtattcc ggccgttaaa cgaaatccgg cc           52

<210> SEQ ID NO 10
<211> LENGTH: 54
<212> TYPE: DNA
<213> ORGANISM: Artificial Sequence
<220> FEATURE:
<223> OTHER INFORMATION: Example nucleotide sequence as illustrated in
      FIG. 7c.

<400> SEQUENCE: 10
taaatcgatt ccggccatta aacgtattcc ggccgttaaa cgaaatccgg cctc         54

<210> SEQ ID NO 11
<211> LENGTH: 52
<212> TYPE: DNA
<213> ORGANISM: Artificial Sequence
<220> FEATURE:
<223> OTHER INFORMATION: Example nucleotide sequence as seen in figure
      7C.

<400> SEQUENCE: 11
taaatcgatt ccggccatta aacgtattcc ggccgttaaa cgaaatccgg cc           52

<210> SEQ ID NO 12
<211> LENGTH: 54
<212> TYPE: DNA
<213> ORGANISM: Artificial Sequence
<220> FEATURE:
<223> OTHER INFORMATION: Example nucleotide sequence as illustrated in
      FIG. 7C.

<400> SEQUENCE: 12
agatttagct aaggccggta atttgcataa ggccggcaat ttgctttagg ccgg         54

<210> SEQ ID NO 13
<211> LENGTH: 42
<212> TYPE: DNA
<213> ORGANISM: Artificial Sequence
<220> FEATURE:
<223> OTHER INFORMATION: Example nucleotide sequence as illustrated in
      FIG. 10A.

<400> SEQUENCE: 13
ggatccttca cgggttaact accaggttct catgggtgat ca                     42

```
<210> SEQ ID NO 14
<211> LENGTH: 42
<212> TYPE: DNA
<213> ORGANISM: Artificial Sequence
<220> FEATURE:
<223> OTHER INFORMATION: Example nucleotide sequence as illustrated in
      FIG. 10A.

<400> SEQUENCE: 14
ggatccaccg ttgacacagt tctcaatatc gaggtatgat ca                             42

<210> SEQ ID NO 15
<211> LENGTH: 41
<212> TYPE: DNA
<213> ORGANISM: Artificial Sequence
<220> FEATURE:
<223> OTHER INFORMATION: Example nucleotide sequence as illustrated in
      FIG. 10A.

<400> SEQUENCE: 15
ggatcctcaa tatcgaggta tcttcacggg ttaactgatc a                              41

<210> SEQ ID NO 16
<211> LENGTH: 42
<212> TYPE: DNA
<213> ORGANISM: Artificial Sequence
<220> FEATURE:
<223> OTHER INFORMATION: Example nucleotide sequence as illustrated in
      FIG. 10B.

<400> SEQUENCE: 16
ggatcccagg ttctcatggg tctcaatatc gaggtatgat ca                             42

<210> SEQ ID NO 17
<211> LENGTH: 42
<212> TYPE: DNA
<213> ORGANISM: Artificial Sequence
<220> FEATURE:
<223> OTHER INFORMATION: Example nucleotide sequence as illustrated in
      FIG. 10B.

<400> SEQUENCE: 17
ggatccttca cgggttaaca cgtagtaccc gtagtatgat ca                             42

<210> SEQ ID NO 18
<211> LENGTH: 41
<212> TYPE: DNA
<213> ORGANISM: Artificial Sequence
<220> FEATURE:
<223> OTHER INFORMATION: Example nucleotide sequence as illustrated in
      FIG. 10B.

<400> SEQUENCE: 18
ggatcctcaa tatcgaggta tcttcacggg ttaactgatc a                              41

<210> SEQ ID NO 19
<211> LENGTH: 58
<212> TYPE: DNA
<213> ORGANISM: Artificial Sequence
<220> FEATURE:
<223> OTHER INFORMATION: Example nucleotide sequence as illustrated in
      FIG. 10C.

<400> SEQUENCE: 19
caccgttgac acagttctca atatcgaggt atscttcacg ggttaactac caggttct            58
```

```
<210> SEQ ID NO 20
<211> LENGTH: 58
<212> TYPE: DNA
<213> ORGANISM: Artificial Sequence
<220> FEATURE:
<223> OTHER INFORMATION: Example nucleotide sequence as illustrated in
      FIG. 10C.

<400> SEQUENCE: 20
catgggtbct caatatcgag gtatscttca cgggttaact acgtagtacc cgtagtat       58
```

MICROFLUIDIC LAB-ON-A-CHIP FOR GENE SYNTHESIS

CROSS-REFERENCE

This application claims priority to U.S. Provisional application No. 62/889,400 filed Aug. 20, 2019 and titled "DNA Storage Write Architecture," which is incorporated herein by reference for all purposes.

This application incorporates by reference the nucleotide sequences in the ASCII text file titled "STL075025_Sequence_Listing_ST25.txt," the date of creation of this ASCII text file being Jul. 16, 2020, and the size of the ASCII text file in bytes being 5 KB, the content of which is incorporated by reference, in its entirety, into this application. The ASCII text file refers to the sequences shown in the figures, particularly, in FIGS. 1A and B, FIG. 2, FIG. 5C, FIG. 7C, and FIGS. 10A, 10B and 10C, where "A" refers to adenine, "G" refers to guanine, "C" refers to cytosine, and "T" refers to thymine. No new matter is being added to this application by addition of these sequence listings.

BACKGROUND

There is always a desire for more data storage and increased writing to and reading from that storage.

DNA is an emerging technology for data storage. Current methods assert that a DNA strand or gene, to store 5 KB of data, can be written in 14 days. Comparatively, magnetic disk drives and magnetic tapes both can write 1 TByte in about an hour. A single DNA base pair location can store 2 bits; thus, 4000 Giga-base pairs would need to be stored in an hour to match the capabilities of a single disk drive or tape. Although current technology is believed to be capable of writing 15 base pairs an hour, there needs to be an 8 to 9 order of magnitude improvement in order for DNA data storage to be viable.

SUMMARY

This disclosure is directed to methods of building DNA strands, or genes, at a high rate, on a small scale.

One particular implementation described herein is a microfluidic lab-on-a-chip for a DNA gene system. The lab-on-a-chip includes a hydrophobic fluidic platform comprising a plurality of arrays operably connected to a voltage source and a controller for the voltage source, a set of first inlets operably connected to the fluidic platform, each first inlet for one DNA symbol from a DNA symbol library, a set of second inlets operably connected to the fluidic platform, each second inlet for one DNA linker from a DNA linker library, and a mixing area operably connected to the fluidic platform and to the plurality of first inlets and the plurality of second inlets. The lab-on-a-chip can also include a PCR station operably connected to the fluidic platform and to the plurality of first inlets and the plurality of second inlets, the PCR station comprising a well of PCR chemicals. In some implementations, the PCR chemicals include only one primer.

Another particular implementation described herein is a method of synthesizing a DNA gene on a lab-on-a-chip. The method includes moving, via voltage, a plurality of DNA symbols from a first set of inlets and a plurality of DNA linkers from a second set of inlets across a hydrophobic fluidic platform and combining on the platform multiple ones of the plurality of DNA symbols with multiple twos of the plurality of DNA linkers to form multiple oligos, and moving, via voltage, the multiple oligos across the platform to form the gene in a mixing area.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. These and various other features and advantages will be apparent from a reading of the following detailed description.

BRIEF DESCRIPTION OF THE DRAWING

The described technology is best understood from the following Detailed Description describing various implementations read in connection with the accompanying drawing.

FIG. 1A is a schematic rendering of two DNA oligos; FIG. 1B is a schematic rendering of the two DNA oligos having overhanging ends; and FIG. 1C is a schematic rendering of the two DNA oligos having overhanging ends joined.

FIG. 5A is a schematic rendering of three oligo symbols, a first step in a method of making a data storage gene; FIG. 5B is schematic rendering of a second step of joining the three symbols each with two linkers, the second step in the method; and FIG. 5C is a schematic rendering of a third step of the method of making a data storage gene.

FIG. 7C is a schematic rendering of the joined symbols from FIG. 7B, a third step of the method of making a data storage gene; and FIG. 7D is a schematic rendering of symbols of FIG. 7C joined to form the data storage gene, a fourth step of the method.

DETAILED DESCRIPTION

Figure 2:
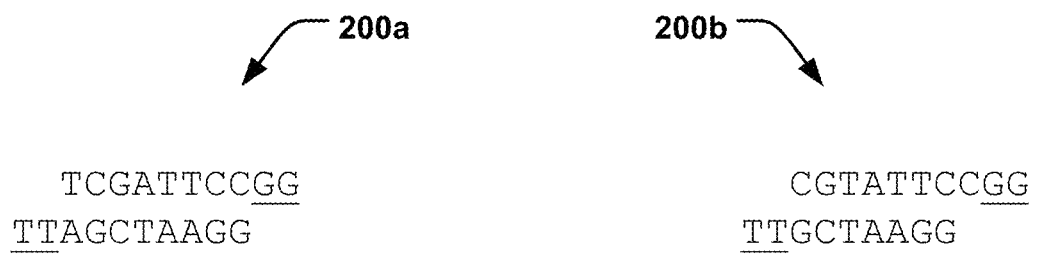
FIG. 2 is a schematic rendering of two DNA oligos both having the same overhanging ends, the DNA oligos being symbols from an example symbol library.

As indicated above, various methods of building DNA strands or genes at a high rate are provided herein. The methods include utilizing libraries of pre-prepared oligos and mass parallelization to form the desired DNA structure or gene. If the gene is to be used as a data storage gene, the methods include assigning a bit pattern (e.g., 00, 01, 10, 11) to each nucleotide (A, C, G, T), thus providing a gene encoding the desired data. It is noted that the methods described herein are directed to synthesizing a data storage gene, however the same methods are applicable to other applications that warrant DNA synthesis.

In the following description, reference is made to the accompanying drawing that forms a part hereof and in which is shown by way of illustration at least one specific implementation. The following description provides additional specific implementations. It is to be understood that other implementations are contemplated and may be made without departing from the scope or spirit of the present disclosure. The following detailed description, therefore, is not to be taken in a limiting sense. While the present disclosure is not so limited, an appreciation of various aspects of the disclosure will be gained through a discussion of the examples, including the figures, provided below. In some instances, a reference numeral may have an associated sub-label consisting of a lower-case letter to denote one of multiple similar components. When reference is made to a reference numeral without specification of a sub-label, the reference is intended to refer to all such multiple similar components.

As indicated above, for a data storage gene, each nucleotide is assigned a bit pattern. In one example, A=00, C=10, G=01, and T=11. Multiple nucleotides form an oligo, and multiple oligos can be combined to eventually form a gene.

In accordance with the system described herein, multiple oligos are grouped in a library. An example of an oligo library is provided in Table 1, which lists pairs of nucleotides and a corresponding binary pattern.

TABLE 1

| DNA Oligo | Binary |
| --- | --- |
| AA | 0000 |
| AG | 0001 |
| AC | 0010 |
| AT | 0011 |
| GA | 0100 |
| GG | 0101 |
| GC | 0110 |
| GT | 0111 |
| CA | 1000 |
| CG | 1001 |
| CC | 1010 |
| CT | 1011 |
| TA | 1100 |
| TG | 1101 |
| TC | 1110 |
| TT | 1111 |

Using the example in Table 1 above, AA is 0000; the two base pair oligo stores 4 bits. As the oligo strand lengthens, more bits, bytes and data can be stored. For example, an oligo that is 8 base pairs long stores 16 bits, or 2 bytes. Using the example in Table 1, an oligo AATTAGTC is 0000111100011110, storing two bytes. It is noted that the example in Table 1 is an example of a primitive case and other bit mappings are possible where both the mapping and number of nucleotides per bit are different.

As indicated above, the system described herein utilizes libraries of oligos to synthesize DNA strands or genes. The system includes a first library of oligos that are referred to herein as "symbols" and a second library of oligos that are referred to herein as "linkers." In general, when a symbol is used in synthesizing a data storage gene, the term "symbol" is used to represent an oligo that has a bit pattern. Additional details regarding symbols and linkers are provided below.

As seen from above, longer chain oligos (symbols and/or linkers) encode more data. Longer chains, however, typically require longer synthesis time. To decrease the time to synthesize longer chains, larger starting oligos can be used in the libraries.

For example, if the library has symbols that are 8 base pairs long, the system can store 16 bits per symbol. Having a DNA symbol library with larger symbols speeds up the synthesis time, but the number of symbols may not scale well. For symbols that are 8 base pairs long, the system would have 65,536 unique symbols in the library. For symbols that are 9 base pairs long, the system would have 262,144 unique symbols in the library. For symbols that are 10 base pairs long, the system would have 1,048,576 unique symbols. As shown in Table 2, the symbol library size is 4 to the power of the base pairs; i.e., the library size is 4^(base pairs per symbol).

TABLE 2

| Base Pairs per Symbol | Number of Bits per Symbol | Size of Symbol Library |
| --- | --- | --- |
| 1 | 2 | 4 |
| 2 | 4 | 16 |
| 3 | 6 | 64 |
| 4 | 8 | 256 |
| 5 | 10 | 1024 |
| 6 | 12 | 4096 |
| 7 | 14 | 16,384 |
| 8 | 16 | 65,536 |
| 9 | 18 | 262,144 |
| 10 | 20 | 1,048,576 |

To form a DNA strand or gene of sufficient length to store usable amounts of data, multiple DNA symbols (i.e., at least two, often at least ten, more often at least twenty) from the library are combined. To control the connection of the symbols to obtain the desired nucleotide sequence, the symbols are provided with overhanging ends.

The overhanging ends can be generated using an isothermal buffer, an exonuclease (such as T5), a DNA ligase (such as Taq) and a DNA polymerase (e.g., a Gibson recipe). With such a procedure, a number of bases from the 5' ends of the symbol (oligo) are removed, creating the overhanging ends. The overhanging ends are complementary pairs; only ends which are complementary will combine when the symbols are combined. FIGS. 1A, 1B and 1C illustrate removal of the ends to provide hanging ends and then combination of two such symbols.

In FIG. 1A, a first symbol precursor 10a and a second symbol precursor 10b are shown. Each of these symbol precursors 10 is a DNA fragment, or oligo, formed of complementary nucleotide pairs. In the particular example shown, each symbol precursor 10 is 20 pairs; other examples of symbol precursors can be shorter or longer.

In FIG. 1B, the two symbol precursors are now shown as a first symbol 100a and a second symbol 100b, each having nucleotides removed therefrom to form an overhanging end at each end. Specifically, the first symbol 100a has a first hanging end 102a and an opposite second hanging end 104a, and the second symbol 100b has a first hanging end 102b and an opposite second hanging end 104b. In the particular example shown, each overhanging end is three nucleotides; other examples of hanging ends can be shorter or longer, in most implementations however, longer. It is these symbols 100, plus many others, that form the symbol library.

In FIG. 1C, the two symbols 100 from FIG. 1B are shown joined, resulting in a longer, combined symbol or oligo 1000; for ease, a delineation between the two symbols 100 is shown in the oligo 1000. In this schematic, the exposed second end 104a of the first symbol 100a is the complement of the exposed first end 102b of the second symbol 100b, thus, the ends 104a, 102b join, resulting in the larger symbol 1000.

In the example shown in FIG. 1B, the hanging end 102 is not the same as the hanging end 104 for each symbol 100, nor is the first hanging end 102a of the first symbol 100a the same as or complimentary to the first hanging end 102b of the second symbol 100b, nor is the second hanging end 104a of the first symbol 100a the same as nor complementary to the second hanging end 104b of the second symbol 100b. The second hanging end 104a of the first symbol 100a is, however, complementary to the first hanging end 102b of the second symbol 100b, in this example. In alternate implementations, the symbols in the symbol library are designed to all have the same overhanging first end and the same overhanging second end. FIG. 2 shows two examples of symbols 200, as symbol 200a and symbol 200b, from a 16-bit symbol library, which have overhanging TT and GG ends (underlined in the figure). In the particular example shown, each overhanging end is two nucleotides; other examples of hanging ends can be shorter or longer, in most implementations however, longer. Further, in other examples, the overhanging ends could be any nucleotides in any sequence, e.g., AA, AC, TCG, etc., as long as the overhanging ends are not complimentary to each other.

By having all the oligos in the symbol library have the same beginning and same end, the same PCR (polymerase chain reaction) chemistry can be used to amplify and/or replenish the inventory in the library Because the ends are the same, the same two primers can be used for every symbol in the PCR process. Additional details regarding replenishing the inventory are provided below.

Figure 3A:
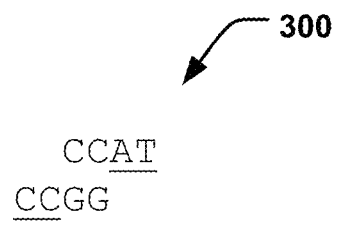
FIG. 3A is a schematic rendering of a DNA oligo having two overhanging ends, the oligo being a linker from an example linker library.

By having the hanging ends being the same for all the symbols 200, the symbols 200 cannot join, as they did in the example shown in FIGS. 1B and 1C. Thus, in accordance with this disclosure, a linker library is provided, which is a collection of "linking" oligos that will attach to the first end and to the second end of all the symbols in the symbol library, thus providing a controlled connection mechanism for the symbols. The linkers are oligos having at least one overhanging end complementary to an overhanging end of the symbol; the linker oligos can be shorter than the symbol oligos. For example, if the overhanging ends for all the symbols 200 are TT and GG, then all the linkers have at least one overhanging end, either AA or CC, complementary to an overhanging end of the symbol; the other end of the linker may be any nucleotide sequence and overhanging or not, pursuant to the discussion below regarding FIG. 4. FIG. 3A illustrates an example linker 300 having two overhanging ends CC and AT (shown underlined); these ends, and thus the linker 300, would join to a symbol having a GG end of to a symbol having a TA end. With these complementary linkers, the symbols assemble in the correct order to form the final data storage gene.

As used and described herein, a DNA storage gene is a collection of DNA symbols connected by linkers. In some implementations only the term "gene" is used to refer to the DNA storage gene.

Figure 3B:
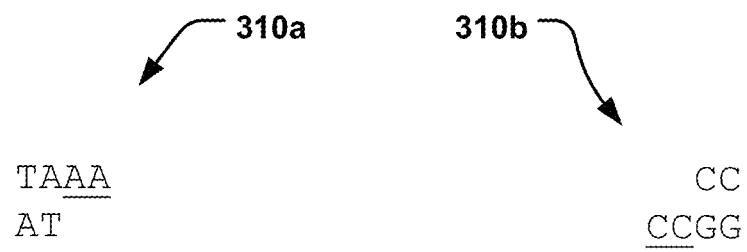
FIG. 3B is a schematic rendering of two DNA oligos having one overhanging end and one terminating end, the DNA oligos being linkers from an example linker library.

In order to obtain the correct length of the resulting data storage gene and also the correct assembly order of the symbols, the linker library includes linkers having terminating or non-overhanging ends. FIG. 3B shows two linkers 310a, 310b, each having one overhanging end (shown underlined in the figure) and one terminating or non-overhanging end. Two linkers 310, each having a terminating end, will cap a chain of assembled symbols, with one linker 310 at each end of the symbols, and will thus terminate the data storage gene. In the shown example of FIG. 3B, for the linker 310a, the overhanging AA end will engage with a TT overhanging end of a symbol and the terminating end of the linker 310a will terminate the gene by not allowing joining to a further symbol or linker at that end. Similarly, for the linker 310b, the overhanging CC end will engage with an overhanging GG end of a symbol and the terminating end of the linker 310b will terminate the other end of the gene.

Figure 4:
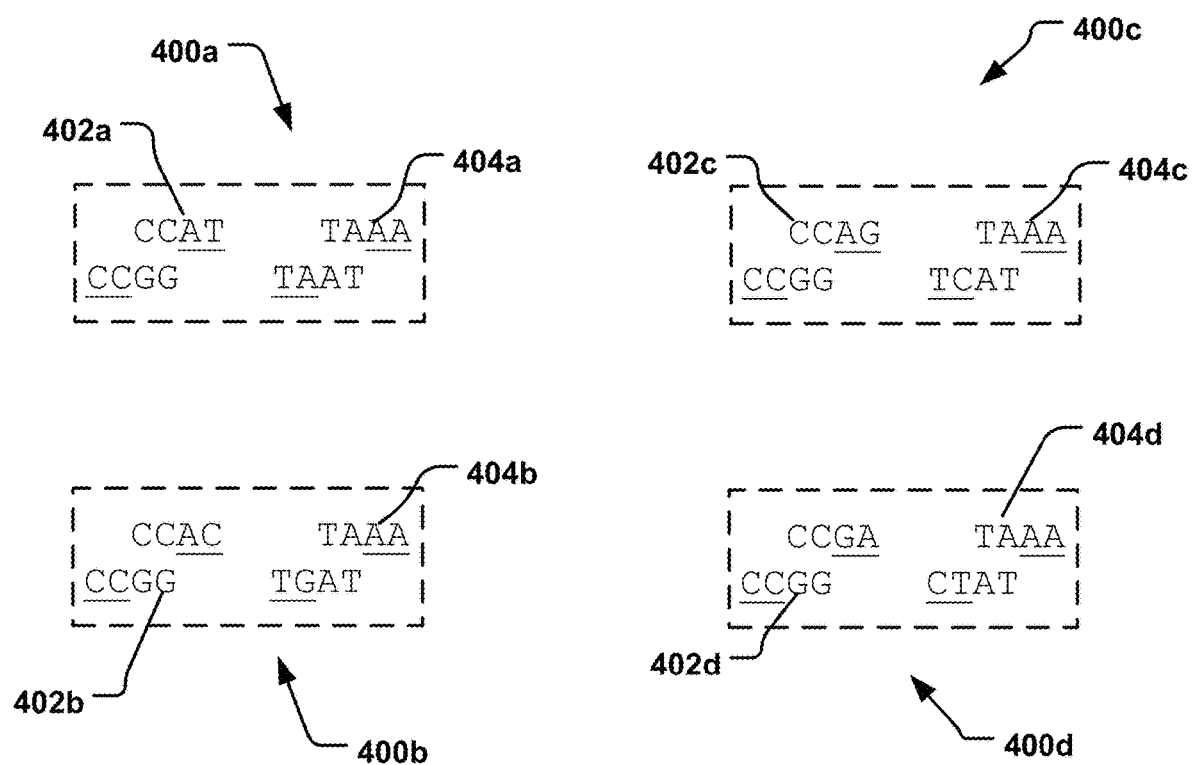
FIG. 4 is a schematic rendering of four example pairs of linkers.

The linkers 300 having two overhanging ends can be provided as pairs, so that at least one of the overhanging ends of each linker is complementary to an overhanging end of the other linker. FIG. 4 provides four examples of linker pairs 400a, 400b, 400c, 400d. Each of these pairs 400 has two linkers, a first linker 402 and a second linker 404, that can be connected to each other, in this implementation, in only one configuration. In the particular example of pairs 400a, 400b, 400c, 400d shown, each of the first linkers 402a, 402b, 402c, 402d has an overhanging CC end and an opposite overhanging end of varying nucleotides (AT for the linker 402a, AC for the linker 402b, AG for the linker 402c, GA for the linker 402d), and each of the second linkers 404a, 404b, 404c, 404d has an overhanging AA end and an opposite overhanging end of varying nucleotides (TA for the linker 404a, TG for the linker 404b, TC for the linker 404c, CT for the linker 404d) that are complementary to the varying end of the first linkers 402. The overhanging CC end of these first linkers 402 will join to the overhanging GG end of the symbols 200 (of FIG. 2) and the overhanging AA of the second linkers 404 end will join to the overhanging TT end of the symbols 200 (of FIG. 2).

Although only four linker pairs 400 are shown in FIG. 4, several other pairs of linkers are possible. It is noted that for this example, a linker having an overhanging CC end and an opposite overhanging AA end is excluded because it will cause unwanted links.

With the library of symbols and the library of linkers, long strands or genes can be made, such as for data storage. FIGS. 5A, 5B, 5C show steps for an example method using linkers and symbols to form a storage gene.

In FIG. 5A, three symbols 500 from the symbol library are shown as symbols 500a, 500b, 500c. Each of the symbols 500 has two overhanging ends, one end being TT and the other being GG; because of these ends, the symbols 500 will not join to each other.

In FIG. 5B, the three symbols 500 are individually combined with two linkers from the linker library, particularly, a first linker 502 and a second linker 504. The two linkers 502, 504 may be from the same pair (e.g., of FIG. 4) or may be from different pairs. As seen, each first linker 502a, 502b, 502c has a CC overhanging end and a second end that is an overhanging end (for the linker 502a, 502b) or a terminating end (for linker 502c). Each second linker 504a, 504b, 504c has an AA overhanging end and a second end that is an overhanging end (for linker 504b, 504c) or a terminating end (for linker 504a). The symbol 500 and the two linkers 502, 504 combine to form a longer, oligo 506 (specifically, the symbol 500a combines with the linkers 502a, 504a to form oligo 506a; the symbol 500b combines with the linkers 502b, 504b to form oligo 506b; and the symbol 500c combines with the linkers 502c, 504c to form oligo 506c). The symbol 500 may combine with the two linkers 502, 504 simultaneously or sequentially; that is, the two linkers 502, 504 may combine with the symbol 500 at the same time, or one may combine before the other. Although only three reactions are shown progressing in parallel in this example, it is understood that any number of reactions could simultaneously occur, thus increasing the rate of building the final data storage gene.

In FIG. 5C, the oligos 506 from FIG. 5B are combined all together to form a storage gene 508. Because of the various overhanging ends, the oligo 506a, oligo 506b, and oligo 506c will link in the correct order to form the storage gene 508, and because of the terminating ends, no further linking on to the storage gene 508 can occur.

The previous discussion has provided an example utilizing a library of symbols (having overhanging ends) and a library of paired linkers to form a DNA gene or strand with the nucleotides arranged in the desired order. Utilizing multiple symbols and multiple linkers, all of which are predetermined oligos, and utilizing parallel reactions, the synthesis rate of the final gene is greatly improved compared to a de novo gene synthesis where each base pair is added one at a time.

In one particular implementation, the methods of this disclosure utilize a 16-bit symbol library having 65,536 unique DNA symbols (oligos) and a linker library having 17 unique DNA linkers (oligos) having two central base pairs. Such as system can readily create a data storage gene that is 15 DNA symbols long, storing 30 bytes (140 bits) using 120 base pairs. Each symbol is combined with corresponding linkers (e.g., as shown in FIG. 5B); multiple combinations can be done in parallel. The resulting oligos 506 are then mixed to form the DNA data storage gene in a second step (e.g., as shown in FIG. 5C). It is noted that although this is shown as a two-step method, there may be multiple chemistry steps per step.

The rate of synthesis of the gene depends on the number of nucleotide pairs in the symbols and the linkers. If the linkers have three base pairs, the system can combine 63 symbols at one time to create a 126 byte data storage gene that requires two steps. If the linkers have five base pairs, the system can combine 1023 symbols at one time to create a 2048 byte data storage gene that requires two steps. Thus, the linker library provides a mechanism for readily combining the symbols in the desired order to form the data storage gene.

Additionally, the linkers can provide timing and sequence information to the data storage gene. The linkers provide a repetitive pattern at known positions in the data storage gene, as seen in FIG. 6.

Figure 6:
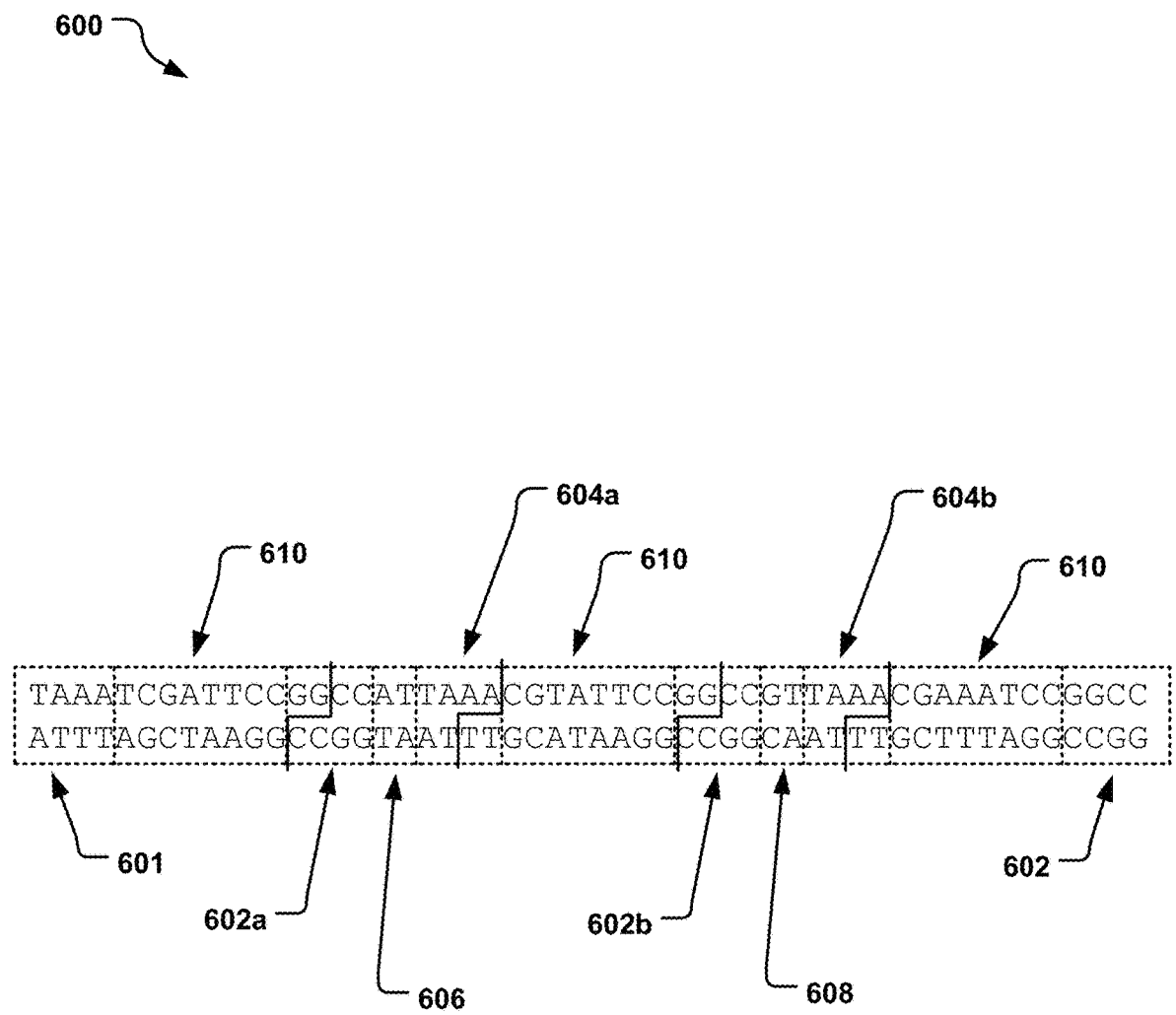
FIG. 6 is a schematic rendering of a data storage gene annotated to show various portions thereof.

In FIG. 6, a data storage gene 600, formed from symbols 610 (specifically, symbols 610a, 610b, 610c) linked via linkers (not called out in FIG. 6), is shown. The storage gene 600 has a unique start sequence 601 at a first end and a unique stop sequence 602 at the second end, both provided by terminated ends on a linker. The linkers provide repeating patterns, in this example a first repeating pattern 602 and a second repeating pattern 604 (both having two occurrences, as pattern 602a, 602b and pattern 604a, 604b). These repeating patterns 602, 604 are at the ends of the linker and can be used for timing recovery. The linkers also provide unique known patterns 606, 608 at the center of the linker. These unique known patterns 606, 608 can be used as address marks in the gene 600. Thus, each linker provides a first repeating pattern 602 (which repeats in all the linkers), a second repeating pattern 604 (which repeats in all the linkers), and a known pattern 606 or 608. The patterns 602, 604, 606, 608, as well as the unique start sequence 601 and the unique stop sequence 602, can additionally be used to identify partial fragments.

The linker library can be designed to reduce the number of linker oligos needed. In such a manner, one linker can be used for multiple connections. In general, the size of the linker library can be limited by having additional steps in the synthesis method.

Figure 7A:
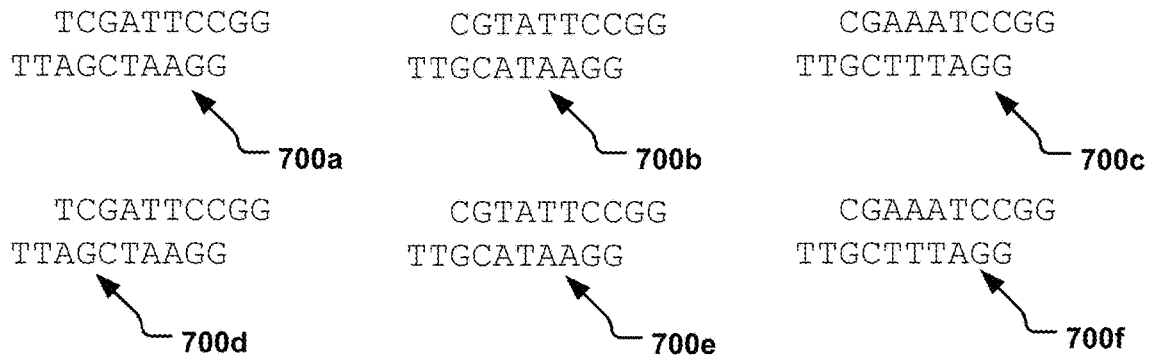
FIG. 7A is a schematic rendering of six oligo symbols, a first step in a method of making a data storage gene.

FIG. 7A through 7D show example steps for making a data storage gene with recycling of the linker library. In FIG. 7A, six symbols 700a, 700b, 700c, 700d, 700e, 700f are shown. Each of these symbols 700 has overhanging ends that are the same for each symbol 700.

Figure 7B:
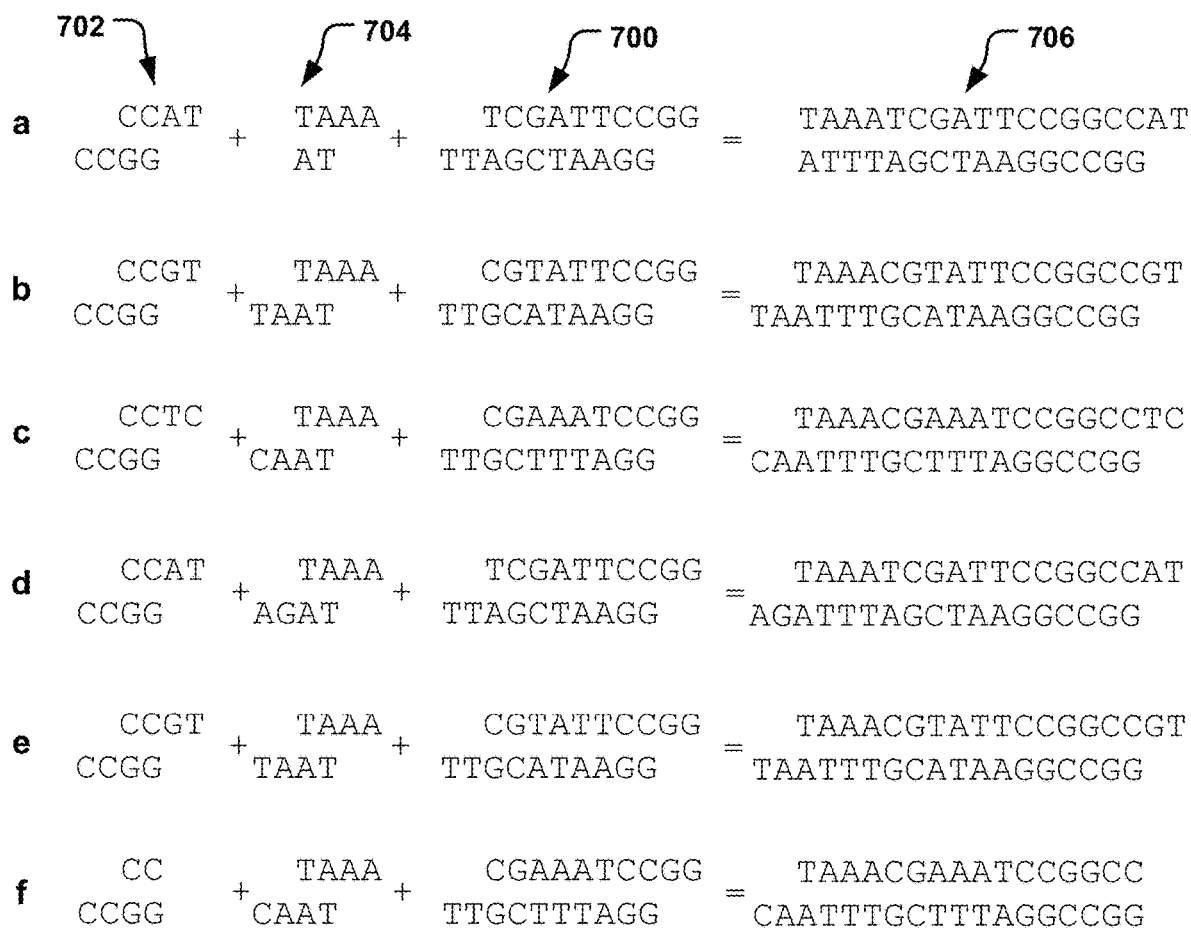
FIG. 7B is schematic rendering of a second step of joining the six symbols each with two linkers, the second step in the method.

In FIG. 7B, the six symbols 700 are individually combined two linkers from the linker library, particularly, a first linker 702 and a second linker 704. The two linkers 702, 704 may be from the same pair (e.g., of FIG. 4) or may be from different pairs. As seen, each first linker 702 has a CC overhanging end. Linkers 702a, 702b, 702c, 702d and 702e have a second end that is an overhanging end of various nucleotides, except that the ends are the same for linkers 702a and 702d, for linkers 702b and 702e. The linker 702f has a truncated or terminating second end. Each second linker 704 has an AA overhanging end. Linkers 704b, 704c, 704d, 704e and 704f have a second end that is an overhanging end of various nucleotides, except that the ends are the same for linkers 704b and 704e, and for linkers 704c and 704f. The linker 704a has a truncated or terminating second end.

The symbol 700 and the two linkers 702, 704 combine to form a longer, combined oligo 706 (specifically, symbol 700a combines with linkers 702a, 704a to form oligo 706a; symbol 700b combines with linkers 702b, 704b to form oligo 706b, etc.). Although only six reactions are shown progressing in parallel in this example, it is understood that any number of reactions could simultaneously occur, thus increasing the rate of synthesis.

FIG. 7C shows intermediate oligo 708a formed by linking combined oligo 706a, combined oligo 706b and combined oligo 706c (all from FIG. 7B) directly together via their overhanging ends, and intermediate oligo 708b formed by linking combined oligo 706d, combined oligo 706e and combined oligo 706f directly together via their overhanging ends. The first intermediate oligo 708a has a terminal end due to linker 704a and the second intermediate oligo 708b has a terminating end due to linker 702f.

In FIG. 7D, the intermediate oligo 708a and intermediate oligo 708b are combined to form a data storage gene 710, without the need to use additional linkers due to the complementary overhanging ends.

Depending on the terminal ends of the symbols and the linkers, additional step(s) may be included combining an oligo (e.g., an intermediate oligo) with a pair of linkers to form yet a longer oligo, which is then joined in a subsequent step, such as in FIG. 7D.

Summarized, for a gene that is 64 symbols long, the following methods can be used to synthesize the gene.

Method #1: Step 1: mix 64 oligo symbols with their corresponding linker oligos from the linker library which contains 64 unique pairs of linkers. Step 2: mix all 64 oligos to form the gene.

Method #2: Step 1: mix 16 oligo symbols with their corresponding linker oligos from the linker library which contains 16 unique pairs of linkers. Step 2: mix each of the oligos from step 1 together to form a 16 symbol oligo. Step 3: repeat steps 1 and 2 three more time with 32 additional symbols. Step 4: after step 3, there are 4 oligos that are each 16 symbols long; mix these individually with 4 pairs of linkers. Step 5: combine all 4 oligos from step 4 to create a gene that is 64 symbols long. The repeats of step 1 and step 2 (described in step 3) can be done in parallel.

As can be seen, Method #2 requires more steps, but also utilizes only 16 linkers versus the 64 linkers for Method #1.

Similarly, for a gene that is 60 symbols long, the following methods can be used to synthesize the gene.

Method #1: Step 1: mix 60 oligo symbols with their corresponding linker oligos from the linker library which contains 60 unique pairs of linkers. Step 2: mix all 60 oligos to form the gene.

Method #2: Step 1: mix 15 oligo symbols with their corresponding linker oligos from the linker library which contains 15 unique pairs of linkers. Step 2: mix each of the oligos from step 1 together to form a 15 symbol oligo. Step 3: repeat steps 1 and 2 three more time with 30 additional symbols. Step 4: after step 3, there are 4 oligos that are each 15 symbols long; mix these individually with 4 pairs of linkers. Step 5: combine all 4 oligos from step 4 to create a gene that is 60 symbols long. The repeats of step 1 and step 2 (described in step 3) can be done in parallel.

As can be seen, Method #2 requires more steps, but also utilizes only 15 linkers versus the 60 linkers for Method #1.

With such methods, the numbers of linkers in the linker library can be reduced or limited by utilizing the same overhanging ends and including additional steps in the synthesis method. For example, a 15 linker-pair linker library reused twice will give a 15×15=225 symbol gene in four steps. A 16 linker-pair linker library reused twice will give a 16×16=256 symbol storage gene in four steps; at 2 bytes per symbol, the result is a 512 byte storage gene. As another example, a 64 linker-pair linker library reused twice will give a 64×64=4096 symbol storage gene in four steps; at 2 bytes per symbol, the result is an 8192 byte storage gene. As yet another example, a 4096 linker-pair linker library reused twice will give a 4096×4096=16,777,216 symbol storage gene in four steps; at 2 bytes per symbol, the result is a 33 megabyte storage gene.

In the example provided above, the system has 65,536 unique DNA symbols in the symbol library, each which is 16 bits on 8 base pairs.

Once a data storage gene is formed, the data stored therein, by the sequence of the nucleotides, can be read by known sequencing methods. However, during reading of the data storage gene, errors may occur. By reading one nucleotide base incorrectly, two bit errors are obtained. For example:

Correct read: AATTAGTC translates to 00001111000110
Incorrect read: TATTAGTC translates to 11001111000110

To inhibit incorrect reading, an error correction can be built in to the DNA symbols. With the system described herein, extra base pairs can be added to the symbols to create a Hamming Code; adding extra pairs to the symbols does not increase the size of the library nor slow down the synthesis of the data storage gene. It is noted that the extra base pairs may, however, decrease the read speed of the gene. Hamming Codes are well known in other applications, and additional details regarding same are well known and are not provided herein.

The synthesis method described above can be implemented in any manner, e.g., utilizing various reactors, flasks, beakers, etc. The method is also particularly suited to be done as a microfluidic lab-on-a-chip process.

Lab-on-a-chip is a common term for an integrated circuit ("chip") on which one or several laboratory functions or chemical reactions are done. The chip can be no more than a few square centimeters. Labs-on-a-chip handle extremely small fluid volumes (e.g., measured as pico-liters) and are often called microfluidic systems. In digital microfluidics, the lab-on-a-chip has a hydrophobic "chip platform" on which fluid droplets (e.g., liquid droplets) can be manipulated by precisely controlled voltage application. The platform may have a cover plate covering the fluidic area. By utilizing the feature of surface tension of the fluid on the platform, the fluid can be precisely moved across the platform by voltage applied to the platform, e.g., in a grid.

For the synthesis method described above, the lab-on-a-chip is operably and fluidically connected to the symbol library, with each symbol retained in a well or other liquid storage compartment. Similarly, the lab-on-a-chip is operably and fluidically connected to the linker library, with each linker retained in a well or other storage compartment. In some designs, there may be at least 10,000 wells for the symbols, or at least 20,000, or at least 30,000 wells, or at least 65,000 wells. Additionally or alternately, there can be at least 10 wells for the linkers, or at least 15 wells, at least 30 wells, or at least 60 wells.

Using known techniques (e.g., voltage differential on the platform), the dispensed symbols and linkers are moved on (across) the platform and mixed in the desired steps. All mixing of the oligos (e.g., symbols and linkers) can be done on the platform or a dedicated mixing station may be used for one or more of the joining steps, e.g., utilizing heat and/or agitation. In some implementations, the platform may include a controllable reaction facilitator, such as a UV light source, and/or the final mixing station may include a voltage source, e.g., to align the completed gene to aid in collection.

One suitable (physical) size for a lab-on-a-chip is about 20 mm by 20 mm, which is compatible to an 8 inch wafer and could have 785,000 array elements, each array element having controllable voltage independently applied thereto. In some implementations, each well or other storage compartment for the oligos (symbols or linkers) is 10× the size of an array element. This would provide 66,560 wells and leave 119,000 arrays for transport and mixing of the symbols and linkers on the platform.

A stacked or otherwise three-dimensional array of labs-on-a-chip would increase density and decrease required area for the synthesis. A drop elevator could be used to provide synthesis on multiple vertically stacked levels.

A cleaning or decontamination mechanism may be included in the lab-on-the-chip to rinse, wash, or otherwise decontaminate certain or all grid locations that have had or will have a symbol or linker present thereon. For example, an amount (e.g., drop) of cleaning solution (e.g., hydrogen peroxide) can be applied to and moved across the platform to cleanse the platform. In one particular example, the cleaning solution can follow immediately behind a linker or symbol, thus cleaning and decontaminating the surface of any oligo that may remain. In another particular example, the cleaning solution can trace the path the oligo will follow.

Figure 8A:
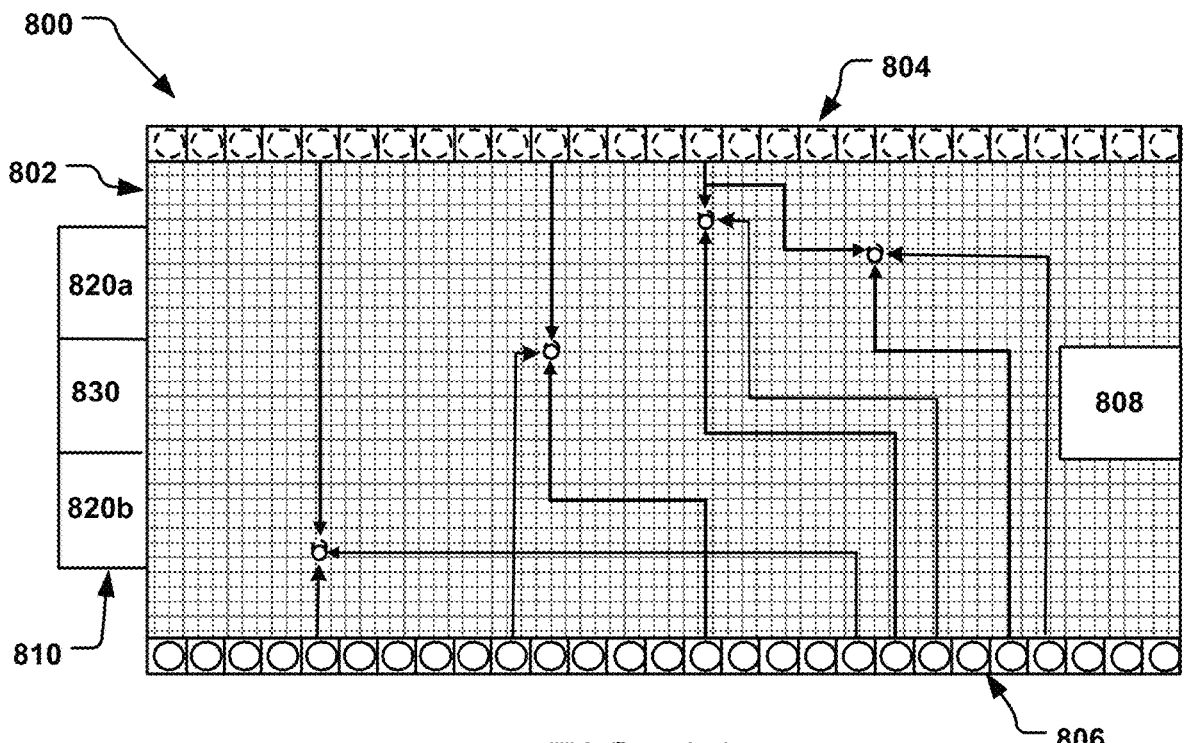
FIG. 8A is a schematic diagram of a lab-on-a-chip showing a step in a method of making a data storage gene.
Figure 8B:
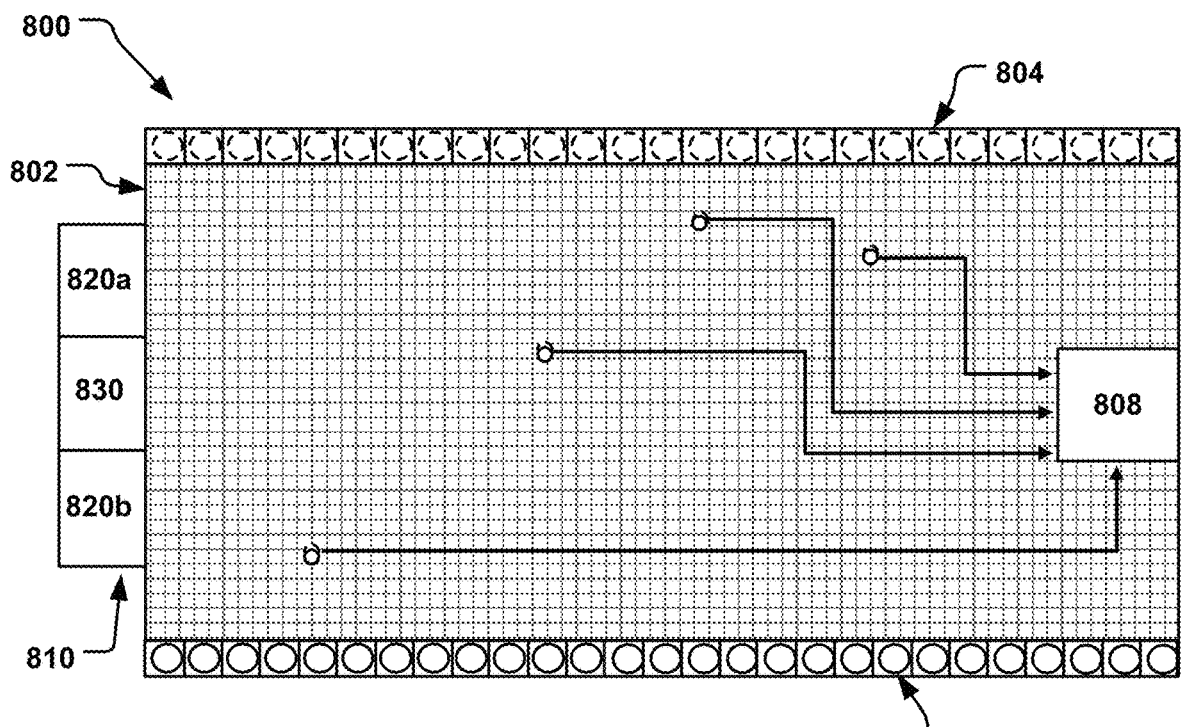
FIG. 8B is a schematic diagram of the lab-on-a-chip showing another step in the method.

FIGS. 8A and 8B illustrate two steps of an example synthesis method. These figures illustrate an example of a lab-on-a-chip to make a 2048 byte storage gene using the methods of this disclosure.

FIGS. 8A and 8B show a lab-on-a-chip 800 with a platform working surface 802 having numerous cells each configured for independently receiving a voltage. The lab 800 includes a plurality of wells 804 for the oligo symbol library, each well 804 retaining one symbol. The lab 800 also includes a plurality of wells 806 for the oligo linker library, each well 806 retaining one linker. Although the figures show the wells 804 and the wells 806 on opposite sides of the platform 802, because there may be significantly more symbol wells 804 than linker wells 806, the wells 804, 806 may be arranged on the chip 800 in any order. To make a 2048 byte gene, 65,536 symbols are present in the wells 804 and 1024 linker pairs (thus, 2048 linker oligos) are present in the wells 806. The lab 800 also has a final mixing location 808 for the final mixing or synthesis step for the data storage gene.

In a first step, partially shown in FIG. 8A, all 1024 linker pairs are combined with their corresponding 1024 (of the 65,536) symbols on the platform 802; for clarity of understanding and to simplify the figure, FIG. 8A shows only four combinations of three unique symbols with eight unique linkers, although all linkers and symbols may eventually be combined on the platform 802. The selected symbol is moved via voltage on the platform 802 to meet and combine with the appropriate linkers (also moved via voltage on the platform 802). In a second step, shown partially in FIG. 8B, all 1024 drops (which have a symbol with two linkers) are moved via voltage to the final mixing location 808 where they self-assemble to form the 2048 byte data storage gene; for clarity of understanding and to simplify the figure, FIG. 8B shows the four combinations moving to the final mixing location 808, although all combined linkers and symbols will eventually move to the final mixing location 808. It is noted that a particular symbol and/or particular linkers may be used multiple times to form the eventual gene. Additionally, a particular symbol can be combined with different linkers, as well as a particular symbol can be combined with different linkers.

The lab 800 also includes a PCR region 810 to replenish the linker and/or symbol libraries, the PCR region 810 including wells for PCR chemicals 820a, 820b and a PCR station 830. Naturally, the symbols and linkers are depleted with each synthesized storage gene. Occasionally, the symbols and linkers need to be replenished; the PCR region 810 of the lab 800 allows this replenishment to be done at the lab 800.

Depending on the symbols and the linkers used (particularly, the overhanging ends of the symbols and the linkers), the same PCR chemistry set can be used for both the symbol and linker libraries. In some implementations, only a few (e.g., one, two, three, or four) PCR chemicals are needed.

Because of the need to move numerous symbols and linkers to each other, to the final mixing location 808, and to the PCR region 810, many of which are moved or moving simultaneously, numerous paths are used. For example, at a point in time, one hundred symbols and 200 linkers (e.g., 16 unique linker pairs, some of which are used multiple times) may be moving on the platform 802. In most implementations, these paths are not constrained by channels or other physical or set paths on the platform 802, but movement of the fluids on the platform 802 is controlled merely by the applied voltage. It is noted that due to the large number of paths needed, a very detailed and complicated traffic map may be needed.

Figure 9:
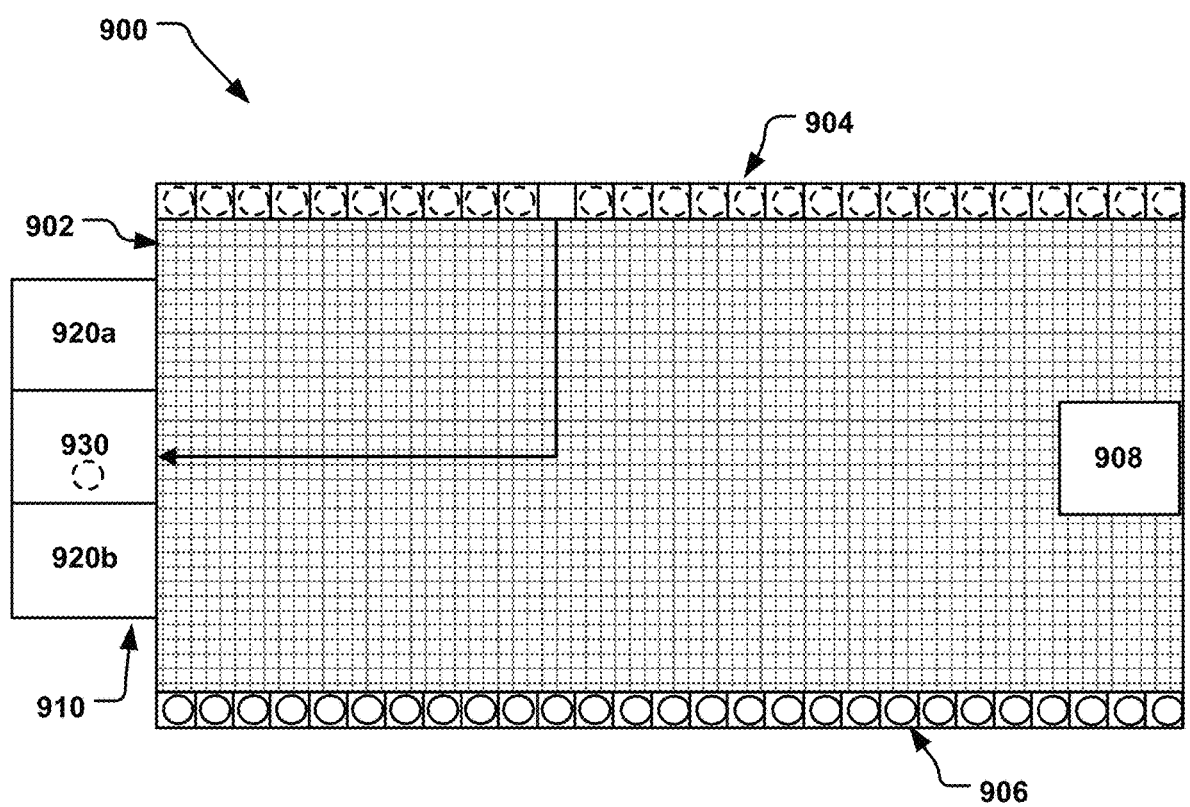
FIG. 9 is a schematic diagram of a lab-on-a-chip showing a PCR process.

FIG. 9 illustrates use of the PCR region to replenish a symbol. Similar to the lab 800, in FIG. 9 the lab-on-a-chip 900 has a platform working surface 902 having numerous cells each configured for independently receiving a voltage. The lab 900 includes a plurality of wells 904 for the oligo symbol library, a plurality of wells 906 for the oligo linker library, and a final mixing location 908. The lab 900 also includes a PCR region 910 to replenish the linker and/or symbol libraries when needed, the PCR region 910 including wells 902a, 902b for PCR chemicals and a PCR station 930.

In FIG. 9, a symbol is shown being moved from its respective well 904 to the PCR station 930. Appropriate PCR chemicals (e.g., primers, DNA polymerase, free nucleotides) are added from the chemical wells 920 to the station 930 to synthesize additional copies of the symbol. The lab 900 can include an appropriate heating source to denature the symbol or linker being synthesized. Additionally, the lab 900 can include an appropriate cooling source for annealing primers to the denatured symbol or linker. The PCR station 930 is configured to include all chemicals needed to automatically and autonomously replenish the symbols and linkers when needed.

In a PCR process, two primers are needed for each oligo, one primer for each end. As indicated above, by having all the oligos in the symbol library have the same beginning and same end (TT and GG overhanging ends, in the example shown), the same PCR chemistry (i.e., the same two primers) can be used for all symbols in the library. In the example provided above however, half of the oligos in the linker library have the same first end and the other half of the oligos in the linker library have another same first end; the second end is different. For the linkers, the same PCR chemistry (i.e., the same primer) can be used for one end of all the linkers; only the second end of the linkers will need a different primer.

To avoid the need for numerous primer chemistries, the oligos and the primer can be specifically designed for each other. In the following example shown in FIGS. 10A, 10B and 10C, a universal primer for all DNA symbols, linkers, and terminating ends is used for PCR amplification.

In these figures, a forward primer "PF", and a reverse primer, "PR" are complimentary to the 3' ends of each DNA oligo (the oligo being a symbol, linker, or terminating end and found at the center region of each oligo, further discussed below). During PCR amplification, primer PF anneals to the forward 3' end and primer PR anneals to the reverse 3' end.

Figure 10A:
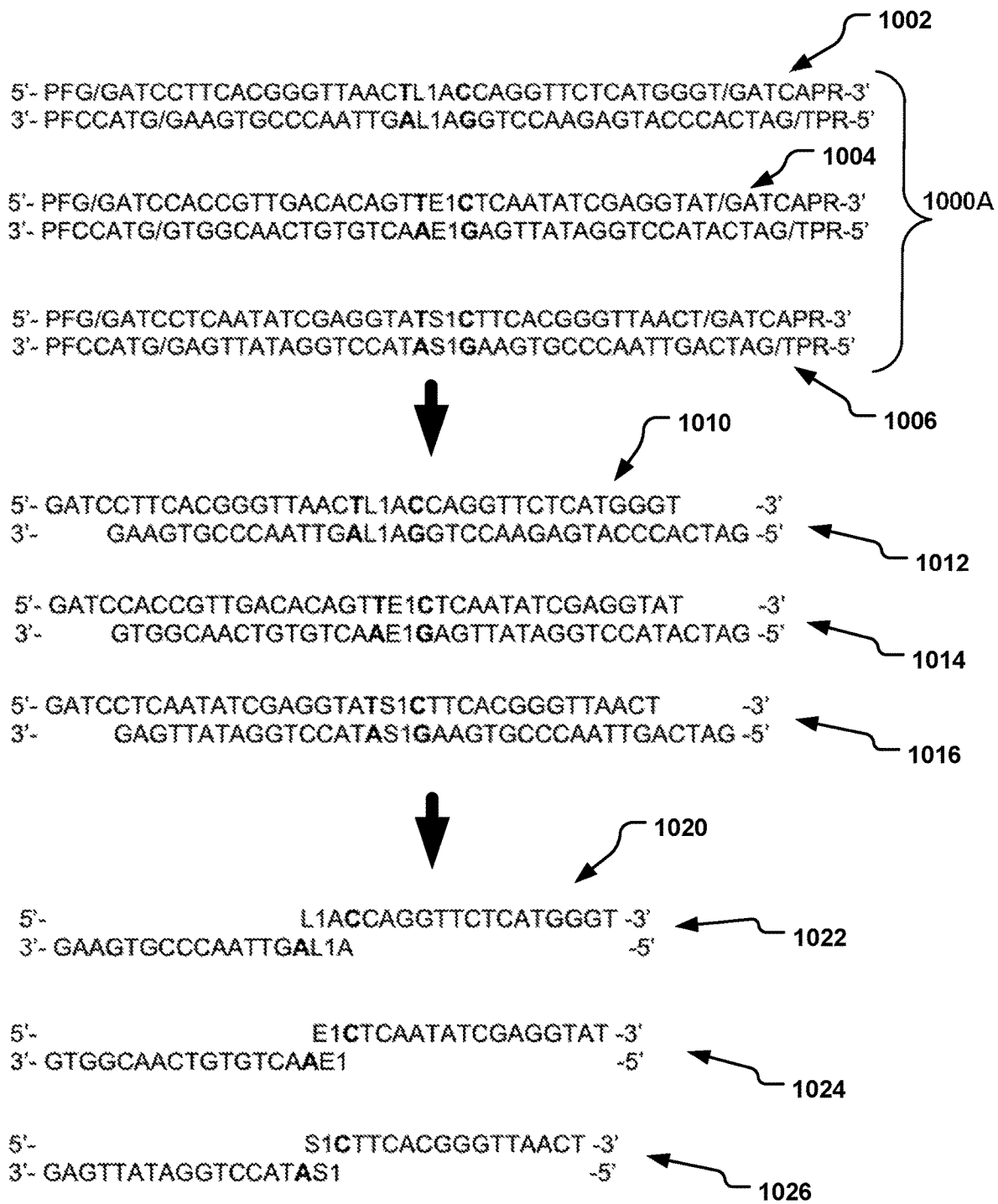
FIG. 10A is a schematic rendering of a first portion of a PCR process utilizing the same primer.
Figure 10B:
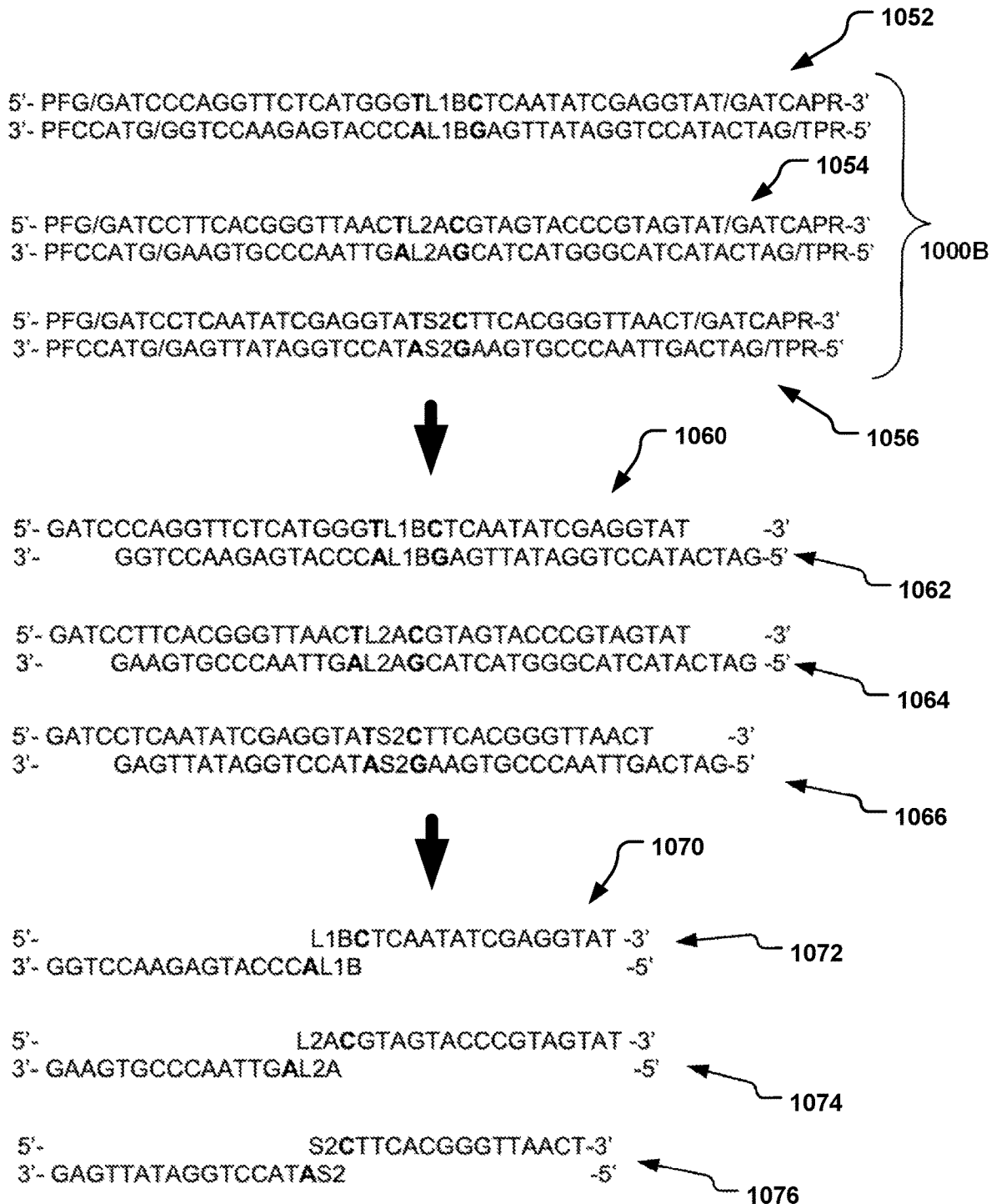
FIG. 10B is a schematic rendering of a second portion of the PCR process.

FIG. 10A and FIG. 10B show these universal primer binding sequences, PR and PF, attached to two reaction sets, one in FIG. 10A and one in FIG. 10B. In FIG. 10A, the set 1000A has an oligo 1002 that contains a linker (linker 1A, depicted as L1A), an oligo 1004 that contains a terminating end (depicted as E1), and an oligo 1006 that contains a symbol (depicted as S1). In FIG. 10B, the set 1000B has an oligo 1052 that contains a linker (linker 1B, depicted as L1B), an oligo 1054 that contains a linker (linker 2A, depicted as L2A), and an oligo 1056 that contains a symbol (depicted as S2). The nucleotides shown in bold in the oligos are necessary internal bases and are adjacent to the linker, symbol, or terminating end.

Downstream of the forward primer PF binding region, there is a restriction enzyme cut site; in the shown example, the cut site is a BamH1 site, identified as

G/GATCC

CCATG/G in each of oligos 1002, 1004, 1006 and oligos 1052, 1054, 1056.

Upstream of the reverse primer PR binding region, there is a second restriction enzyme cut site; in the shown example, the cut site is a Bcl1 site, identified as

T/GATCA

ACTAG/T in each of oligos 1002, 1004, 1006 and oligos 1052, 1054, 1056.

The slashes (/) indicate the locations where the restriction enzymes cut.

The two cut sites, at the forward primer PF and the reverse primer PR, are different in this example but in other implementations the cut sites can be the same.

After PCR amplification, the primer binding regions may be cut off the rest of the DNA segment by the addition of the appropriate restriction enzyme. In FIG. 10A, the oligos 1002, 1004, 1006 are cut at the Bcl1 and BamH1 sites (e.g., by a reaction that takes 5-15 minutes at 37° C.) to form a next set 1010 of oligos, specifically, the oligos 1012, 1014, 1016. Similarly, in FIG. 10B, the oligos 1052, 1054, 1056 are cut at the Bcl1 and BamH1 sites (e.g., by a reaction that takes 5-15 minutes at 37° C.) to form a next set 1060 of oligos, specifically, the oligos 1062, 1064, 1066.

In the example provided above, the cutting reaction takes 5-15 minutes at 37° C. The reaction process may be done at any elevated temperature, e.g., 37° C. or 45° C., dependent on the particular restriction enzyme utilized. After a specified reaction time (e.g., 5-60 minutes), the reaction may be stopped by any known mechanism, including by elevating the temperature further for a specified time (e.g., 65° C. for 5-15 minutes) or the addition of EDTA. Alternatively, if the restriction enzyme reaction does not require a stop step, the stop step may be eliminated. Oligos 1012, 1014, 1016 in FIG. 10A and oligos 1062, 1064, 1066 in FIG. 10B are the resulting DNA segments after the primers are cut off by a Bcl1 and BamH1 restriction digest.

After the primers are removed by the restriction enzyme digest, as described above, the resulting DNA segments (e.g., oligos 1012, 1014, 1016 and 1062, 1064, 1066) may be assembled as previously described, or the DNA segments may be further processed.

A Gibson assembly method can be used to chew back the 5' ends to generate complementary overhangs. The oligos 1012, 1014, 1016 and the oligos 1062, 1064, 1066 of each of the sets 1010, 1060, respectively, can undergo a chewback during a Gibson assembly process to arrive at the set 1020 in FIG. 10A having oligos 1022, 1024, 1026 and the set 1070 in FIG. 10B having oligos 1072, 1074, 1076.

Figure 10C:
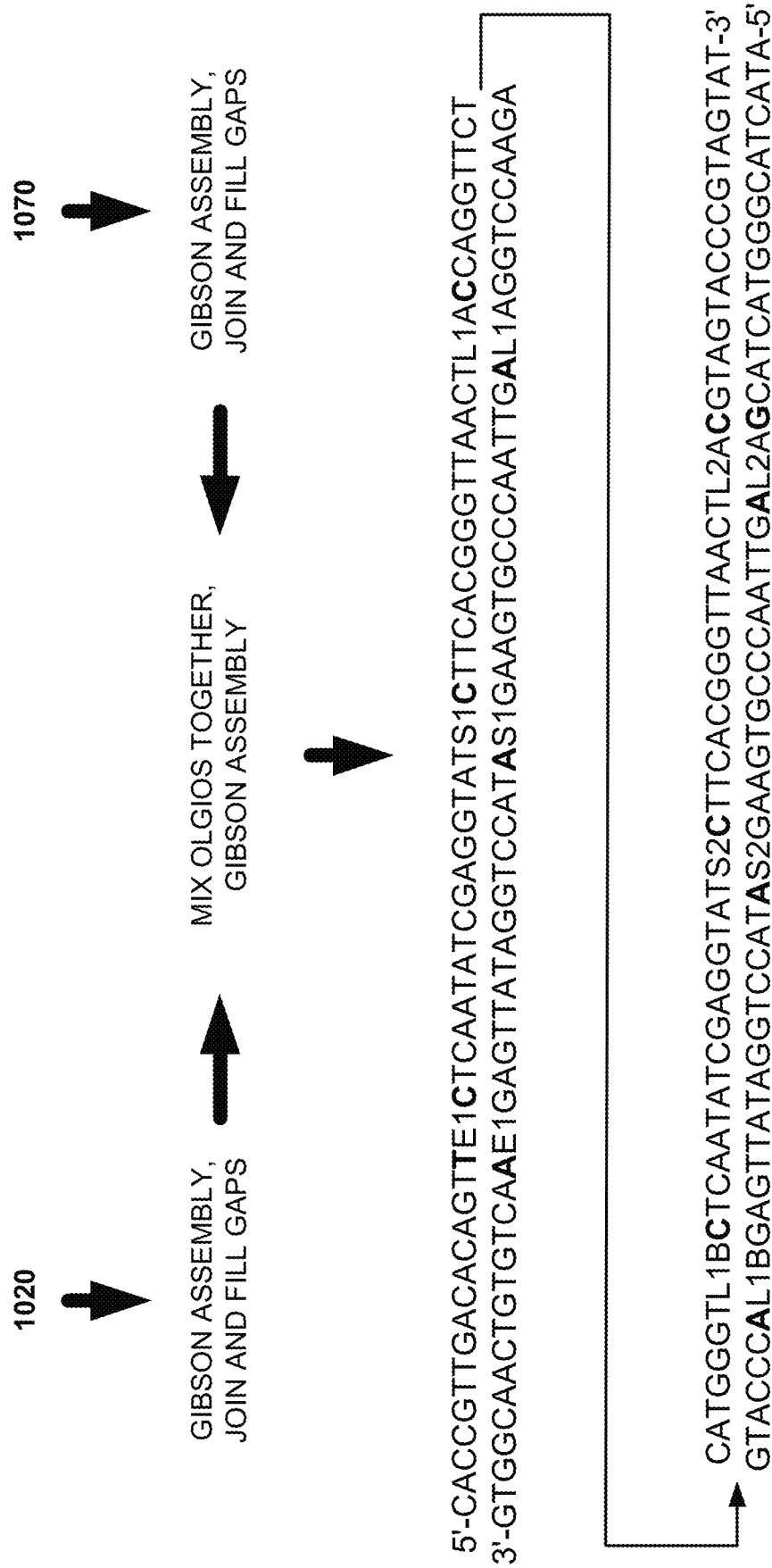
FIG. 10C is a schematic rendering of a portion of an assembly process.

Turning to FIG. 10C, the complimentary overhangs of the DNA segments or oligos of the sets 1020, 1070 can then be joined via Gibson assembly to fill any gaps and generate two storage gene fragments (not shown in FIG. 10C). Subsequently, the two storage gene fragments may be combined in a separate assembly reaction (e.g., Gibson assembly) to form a larger storage gene fragment or a complete storage gene, as shown in FIG. 10C.

It is noted that although not specifically stated, between any of the assembly steps described throughout this description, any additional steps may be added as needed or desired, for example, a PCR amplification step, a purification step, or both. Either of these example steps could be performed after a Gibson assembly step.

The above specification and examples provide a complete description of the structure and use of exemplary implementations of the invention. The above description provides specific implementations. It is to be understood that other implementations are contemplated and may be made without departing from the scope or spirit of the present disclosure. The above detailed description, therefore, is not to be taken in a limiting sense. While the present disclosure is not so limited, an appreciation of various aspects of the disclosure will be gained through a discussion of the examples provided.

Unless otherwise indicated, all numbers expressing feature sizes, amounts, and physical properties are to be understood as being modified by the term "about," whether or not the term "about" is immediately present. Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass implementations having plural referents, unless the content clearly dictates otherwise. As used in this specification and the appended claims, the term "or" is generally employed in its sense including "and/or" unless the content clearly dictates otherwise.

Spatially related terms, including but not limited to, "bottom," "lower", "top", "upper", "beneath", "below", "above", "on top", "on," etc., if used herein, are utilized for ease of description to describe spatial relationships of an element(s) to another. Such spatially related terms encompass different orientations of the device in addition to the particular orientations depicted in the figures and described herein. For example, if a structure depicted in the figures is turned over or flipped over, portions previously described as below or beneath other elements would then be above or over those other elements.

Since many implementations of the invention can be made without departing from the spirit and scope of the invention, the invention resides in the claims hereinafter appended. Furthermore, structural features of the different implementations may be combined in yet another implementation without departing from the recited claims.

What is claimed is:

1. A microfluidic lab-on-a-chip for a DNA gene system, comprising:
a hydrophobic fluidic platform comprising a plurality of array elements, each array element independently operably connected to a voltage source and a controller for the voltage source;
a set of first inlets operably connecting a set of first wells to the fluidic platform;
a set of second inlets operably connecting a set of second wells to the fluidic platform, with a number of second wells and second inlets less than a number of first wells and first inlets;
a DNA symbol library comprising a number of DNA symbols each comprising nucleotide pairs, with each first well containing therein one DNA symbol;
a DNA linker library comprising pairs of DNA linkers each comprising nucleotides, a first linker of a pair having a first overhanging end and a second linker of the pair having a first overhanging end, the first overhanging end of the first linker being the same nucleotide for each first linker, with each second well containing one DNA linker, wherein the first linker of a pair is adapted to join to the first overhanging end of a DNA symbol;
the voltage source configured to move DNA symbols from the first inlets and to move DNA linkers from the second inlets and combine a DNA symbol with two DNA linkers on the fluidic platform to form an oligo;
a mixing area operably connected to the fluidic platform to receive the oligos formed by DNA symbols and two DNA linkers; and
a PCR station operably connected to the fluidic platform and to the plurality of first inlets and the plurality of second inlets, the PCR station comprising PCR chemicals for synthesizing the DNA symbols and the DNA linkers.

2. The microfluidic lab-on-a-chip of claim 1 having a size of about 20 mm×20 mm.

3. The microfluidic lab-on-a-chip of claim 1 having at least 100,000 array elements on the platform.

4. The microfluidic lab-on-a-chip of claim 1 comprising at least 10,000 first wells.

5. The microfluidic lab-on-a-chip of claim 4 comprising at least 20,000 first wells.

6. The microfluidic lab-on-a-chip of claim 5 comprising at least 65,000 first wells.

7. The microfluidic lab-on-a-chip of claim 1 comprising at least 10 second wells.

8. The microfluidic lab-on-a-chip of claim 7 comprising at least 60 second wells.

9. The microfluidic lab-on-a-chip of claim 1 further comprising a decontamination mechanism for the fluidic platform.

10. The microfluidic lab-on-a-chip of claim 1 wherein the PCR station has only one primer.

* * * * *